(12) United States Patent
Tsuda et al.

(10) Patent No.: US 10,656,121 B2
(45) Date of Patent: May 19, 2020

(54) METHOD FOR DETECTING ARRANGEMENT DISORDER OF FIBERS IN CONDUCTIVE COMPOSITE MATERIAL, AND DEVICE FOR DETECTING ARRANGEMENT DISORDER OF FIBERS IN CONDUCTIVE COMPOSITE MATERIAL

(71) Applicant: IHI Corporation, Koto-ku (JP)

(72) Inventors: Akinori Tsuda, Koto-ku (JP); Hiroki Kawai, Koto-ku (JP); Hiroaki Hatanaka, Koto-ku (JP); Yuichi Yamaguchi, Koto-ku (JP); Koichi Inagaki, Koto-ku (JP)

(73) Assignee: IHI Corporation, Koto-ku (JP)

( * ) Notice: Subject to any disclaimer, the term of this patent is extended or adjusted under 35 U.S.C. 154(b) by 53 days.

(21) Appl. No.: 15/765,523

(22) PCT Filed: Jul. 8, 2016

(86) PCT No.: PCT/JP2016/070304
§ 371 (c)(1),
(2) Date: Apr. 3, 2018

(87) PCT Pub. No.: WO2017/061156
PCT Pub. Date: Apr. 13, 2017

(65) Prior Publication Data
US 2019/0079054 A1 Mar. 14, 2019

(30) Foreign Application Priority Data
Oct. 9, 2015 (JP) .................................. 2015-200887

(51) Int. Cl.
*G01R 33/14* (2006.01)
*G01N 27/90* (2006.01)
(Continued)

(52) U.S. Cl.
CPC ........... *G01N 27/9033* (2013.01); *G01B 7/34* (2013.01); *G01N 27/902* (2013.01);
(Continued)

(58) Field of Classification Search
CPC ............... G01N 27/90; G01N 27/9033; G01N 27/9013; G01N 27/72; G01N 27/82;
(Continued)

(56) References Cited

U.S. PATENT DOCUMENTS 7,701,206 B2 * 4/2010 Linder ..................... G01B 7/10
324/227
7,755,351 B2 * 7/2010 Brady ................. G01N 27/9046
324/222

(Continued)

FOREIGN PATENT DOCUMENTS

JP 2-150765 A 6/1990
JP 7-167839 A 7/1995
(Continued)

OTHER PUBLICATIONS

International Search Report dated Sep. 27, 2016 in PCT/JP2016/070304 filed Jul. 8, 2016.
(Continued)

*Primary Examiner* — Thang X Le
(74) *Attorney, Agent, or Firm* — Oblon, McClelland, Maier & Neustadt, L.L.P.

(57) ABSTRACT

Provided are a method and device for detecting arrangement disorder of fibers in a conductive composite material. A coil (7) is disposed at a position at which the coil (7) faces the conductive composite material, and thereby a current can be applied to the conductive composite material. Thus, work or the like for attaching electrodes to the conductive composite material is not required. As a result, the arrangement disorder of the fibers in the conductive composite material can
(Continued)

easily be detected. A method for detecting meandering of fibers in a conductive composite material includes a step of disposing a magnetic field sensor (8) at a position at which the magnetic field sensor (8) faces a surface (Sa) of the conductive composite material such that a direction (D) of a magnetosensitive axis is horizontal with the surface (Sa) and is parallel to coil faces (7e). Therefore, the magnetic field sensor (8) measures a magnetic field, and thereby a portion at which the arrangement disorder of the fibers in the conductive composite material is present can be detected.

9 Claims, 8 Drawing Sheets (51) Int. Cl.
G01B 7/34 (2006.01)
G01N 33/36 (2006.01)
G01N 33/00 (2006.01)
(52) U.S. Cl.
CPC ....... *G01N 27/9013* (2013.01); *G01N 33/367* (2013.01); *G01N 2033/0003* (2013.01)
(58) Field of Classification Search
CPC ............... G01N 33/36; G01N 33/367; G01N 2033/0003; G01N 25/20; G01B 7/34
See application file for complete search history.

(56) References Cited

U.S. PATENT DOCUMENTS

| 2004/0124087 | A1* | 7/2004 | Christ | C04B 35/565 |
| | | | | 205/83 |
| 2008/0174306 | A1 | 7/2008 | Brady | |
| 2012/0126803 | A1 | 5/2012 | Goldfine et al. | |
| 2016/0123928 | A1 | 5/2016 | Kobayashi et al. | |
| 2016/0209365 | A1 | 7/2016 | Tsuda et al. | |
| 2017/0292925 | A1* | 10/2017 | Zhao | G01N 25/20 |

FOREIGN PATENT DOCUMENTS

| JP | 7-229875 A | 8/1995 |
| JP | 9-72884 A | 3/1997 |
| JP | 2000-55844 A | 2/2000 |
| JP | 2000-283964 A | 10/2000 |
| JP | 2006-322860 A | 11/2006 |
| JP | 2008-39394 A | 2/2008 |
| JP | 2015-75447 A | 4/2015 |
| RU | 1647376 A1 | 5/1991 |
| WO | WO 2014/142306 A1 | 9/2014 |
| WO | WO 2015/052956 A1 | 4/2015 |

OTHER PUBLICATIONS

Mizukami, K. et al., "Detection of fiber waviness in CFRP using eddy current testing", Symposium on Advanced Materials and Nondestructive Measurements for the Establishment of a Safe and Secure Society Perspectives for the Next Generation Sensors for Super-High Temperature Environment and Their Industrial Applications Joint Symposium Proceeding, the Japanese Society for Non-Destructive Inspection Division of Non-Destructive Evaluation of New Materials, Mar. 16, 2015, 9 total pages (with English abstract).

Mizukami, K. et al., "Detection of Out-of-plane Fiber Waviness in CFRP Using Eddy Current Testing", Dai 6 Kai Nippon Fukugo Zairyo Kaigi JCCM-6, Mar. 2015, 4 total pages (with English abstract).

Mizukami, K. et al. "Detection of in-plane and out-of-plane fiber waviness in unidirectional carbon fiber reinforced composites using eddy current testing" Composites Part B, Elsevier, vol. 86, XP 029372399, 2015, pp. 84-94.

Mizukami, K. et al. "Detection of in-plane fiber waviness in cross-ply CFRP laminates using layer selectable eddy current method" Composites: Part A, Elsevier, vol. 82, XP 029402630, 2015, pp. 108-118.

* cited by examiner

METHOD FOR DETECTING ARRANGEMENT DISORDER OF FIBERS IN CONDUCTIVE COMPOSITE MATERIAL, AND DEVICE FOR DETECTING ARRANGEMENT DISORDER OF FIBERS IN CONDUCTIVE COMPOSITE MATERIAL

TECHNICAL FIELD

The present disclosure relates to a method for detecting arrangement disorder of fibers in a conductive composite material, and a device for detecting arrangement disorder of fibers in a conductive composite material.

Priority is claimed on Japanese Patent Application No. 2015-200887, filed on Oct. 9, 2015, the content of which is incorporated herein by reference.

BACKGROUND ART

In conductive composite materials in which a plurality of prepregs obtained by impregnating a conductive fiber fabric, for instance, a carbon fiber fabric, with a thermoset resin or a thermoplastic resin are laminated, arrangement disorder of fibers may occur during production. For example, a method for detecting the arrangement disorder of the fibers in the conductive composite material may include ultrasonic testing (e.g., see Patent Literature 1).

CITATION LIST

Patent Literature

[Patent Literature 1] Japanese Unexamined Patent Publication No. H02-150765

SUMMARY

Technical Problem

However, when this ultrasonic testing is adopted, the arrangement disorder of fibers may not be accurately detected according to circumstances of the arrangement disorder of fibers. In place of this method, a method for detecting the arrangement disorder of fibers by attaching electrodes to a specimen, applying a current to the specimen, and detecting a change in magnetic field may be adopted. However, it may be difficult or take much effort to attach the electrodes according to this method. Accordingly, as the method for detecting the arrangement disorder of fibers, an easy detecting method that does not take much effort is required. A detecting method that can be used to accurately detect arrangement disorder of fibers without taking much effort is required.

The present disclosure was made to solve the above problems, and illustrates a method and device for detecting arrangement disorder of fibers in a conductive composite material, which can be used to easily and accurately detect arrangement disorder of fibers in a conductive composite material.

Solution to Problem

A method for detecting arrangement disorder of fibers in a conductive composite material according to an aspect of the present disclosure is a method for detecting arrangement disorder of fibers in a conductive composite material using conductive fibers, and includes: a step of disposing a coil at a position at which the coil faces a surface of the conductive composite material such that a coil face is perpendicular to the surface; a step of disposing a magnetic field measuring unit at a position at which the magnetic field measuring unit faces the surface of the conductive composite material such that a direction of a magnetosensitive axis is horizontal with the surface and is parallel to the coil face; and a step of detecting a portion at which the arrangement disorder of the fibers in the conductive composite material is present by measuring a magnetic field with the magnetic field measuring unit.

Advantageous Effects

According to the aspect of the present disclosure, arrangement disorder of fibers in a conductive composite material can be easily and accurately detected.

DESCRIPTION OF EMBODIMENTS

A method for detecting arrangement disorder of fibers in a conductive composite material according to an aspect of the present disclosure is a method for detecting arrangement disorder of fibers in a conductive composite material using conductive fibers, and includes: a step of disposing a coil at a position at which the coil faces a surface of the conductive composite material such that a coil face is perpendicular to the surface; a step of disposing a magnetic field measuring unit at a position at which the magnetic field measuring unit faces the surface of the conductive composite material such that a direction of a magnetosensitive axis is horizontal with the surface and is parallel to the coil face; and a step of detecting a portion at which the arrangement disorder of the fibers in the conductive composite material is present by measuring a magnetic field with the magnetic field measuring unit.

In this method for detecting meandering of fibers in a conductive composite material, the coil is disposed at a position at which it faces the surface of the conductive composite material such that the coil face is perpendicular to the surface, and thereby eddy currents can be created at the conductive composite material. In addition, the magnetic field measuring unit is disposed at a position at which it faces the conductive composite material, and thereby a magnetic field generated by the eddy currents can be measured. In this way, the coil is disposed at the position at which it faces the conductive composite material, a current can be applied to the conductive composite material. Thus, work or the like of attaching electrodes to the conductive composite material is not required. Accordingly, the arrangement disorder of the fibers of the conductive composite material can be easily detected. Here, as a result of earnest study, the inventors of this disclosure found that the magnetic field measuring unit was disposed such that the direction of the magnetosensitive axis was horizontal with the surface of the conductive composite material and was parallel to the coil face, and thereby the portion at which the arrangement disorder of the fibers in the conductive composite material is present can be accurately detected compared to when the direction of the magnetosensitive axis is set to another direction. The method for detecting arrangement disorder of fibers in a conductive composite material according to the aspect of the present disclosure includes the step of disposing the magnetic field measuring unit at a position at which it faces the surface of the conductive composite material such that the direction of the magnetosensitive axis is horizontal with the surface and is parallel to the coil face. Accordingly, the magnetic field measuring unit measures the magnetic field, and thereby the portion at which the arrangement disorder of the fibers in the conductive composite material is present can be accurately detected. Thus, the arrangement disorder of the fibers in the conductive composite material can be easily and accurately detected.

In any aspect, the magnetic field measuring unit may be provided between the surface of the conductive composite material and the facing coil. Thereby, a distance between the magnetic field measuring unit and the surface of the conductive composite material is reduced, and a change in the magnetic field can be more accurately detected.

In any aspect, an end of the coil which faces the surface of the conductive composite material may extend along the surface. Thereby, the eddy currents caused by the coil is easily created at the conductive composite material.

In any aspect, a frequency of a current flowing to the coil may range from 10 kHz to 20 MHz. Thereby, the eddy currents caused by the coil is easily created at the conductive composite material.

A device for detecting arrangement disorder of fibers in a conductive composite material according to an aspect of the present disclosure is a device for detecting arrangement disorder of fibers in a conductive composite material using conductive fibers, and includes: a coil disposed at a position at which the coil faces a surface of the conductive composite material such that a coil face thereof is perpendicular to the surface; a magnetic field measuring unit disposed at a position at which the magnetic field measuring unit faces the surface of the conductive composite material such that a direction of a magnetosensitive axis is horizontal with the surface and is parallel to the coil face; and a detector for detecting a portion at which the arrangement disorder of the fibers in the conductive composite material is present by measuring a magnetic field with the magnetic field measuring unit.

The device for detecting arrangement disorder of fibers in a conductive composite material can obtain the same operation and effects as the above method for detecting arrangement disorder of fibers in a conductive composite material.

Hereinafter, an embodiment of the present disclosure will be described in detail with reference to the drawings. In the description of the drawings, the same or equivalent elements are designated by the same reference signs, and duplicate description thereof may be omitted.

Figure 1:
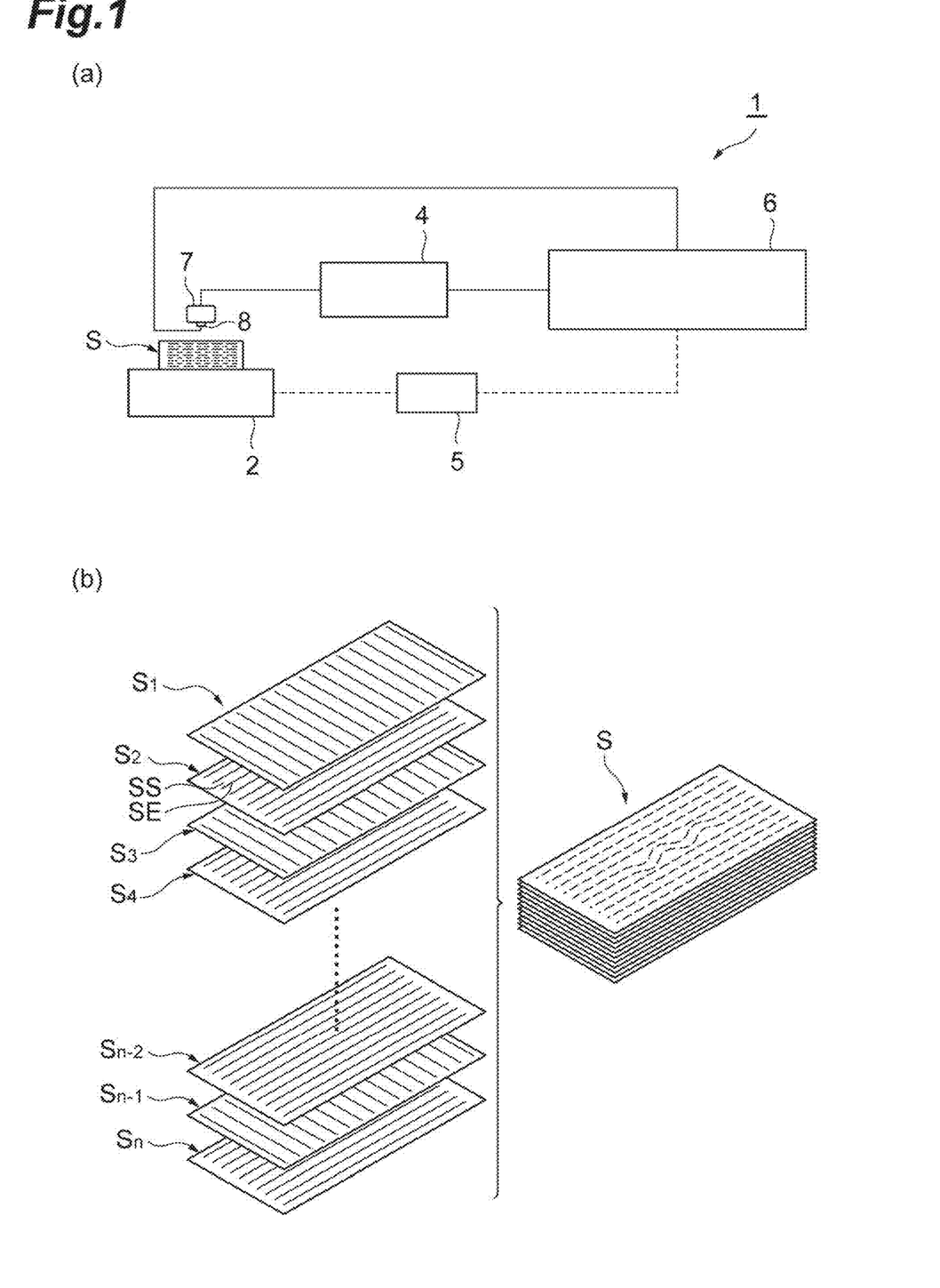
FIG. 1(a) is a diagram illustrating a device for detecting meandering of fibers, which is used to perform a method for detecting meandering of fibers in a conductive composite material according to an embodiment of the present disclosure.
FIG. 1(b) is a perspective diagram illustrating a laminated structure of the conductive composite material.

A device 1 for detecting meandering of fibers illustrated in FIG. 1(a) (a device for detecting arrangement disorder of fibers in a conductive composite material) is a device used to perform a method for detecting meandering of fibers in a conductive composite material (a method for detecting arrangement disorder of fibers in a conductive composite material). As illustrated in FIG. 1(a), the device 1 for detecting meandering of fibers includes a stage 2 on which a specimen S of a conductive composite material is placed, a coil 7 and a magnetic field sensor (magnetic-field measuring means) 8 that are held above the specimen S on the stage 2 at an adequate interval, a current applying unit 4 that applies a current to the coil 7, a driver 5 that drives the stage 2, and a controller 6. The current application to the coil 7 caused by the current applying unit 4 is performed according to an instruction from the controller 6. Likewise, the stage 2 is driven according to an instruction from the controller 6 for the driver 5. Thereby, the coil 7 and the magnetic field sensor 8 are adapted to scan the specimen S. A form of the arrangement disorder of fibers is not particularly limited. In the arrangement of fibers arranged in a constant pattern, a portion at which the pattern collapses due to, for instance, partial flexure of the fibers corresponds to a portion at which the arrangement of the fibers is disordered. The meandering corresponds to a state in which the fibers are bent and thereby undulated. In the present embodiment, the "meandering" is detected as an example of the "arrangement disorder of the fibers in the conductive composite material," and a description of the present embodiment is based on this.

In this case, as illustrated in FIG. 1(b), the specimen S is molded in a cuboidal shape by alternately laminating a plurality of prepregs $S_1, S_3, \ldots, S_{n-1}$, and $S_2, S_4, \ldots, S_n$, in which a conductive fiber fabric SS is impregnated with a thermoplastic resin or a thermoset resin, and there is a difference of 90° between directions of fiber orientation. In the present embodiment, to allow the current to flow in directions (shown longitudinal directions) of conductive fibers SE, which act as targets for checking whether the meandering is present, in the conductive fiber fabric SS of each of the plurality of prepregs $S_2, S_4, \ldots, S_n$ among the plurality of prepregs $S_1$ to $S_n$ in the specimen S, the coil 7 is disposed at a position at which it faces a surface of the specimen S as illustrated in FIG. 2(a), and a current is applied to the coil 7.

Figure 2:
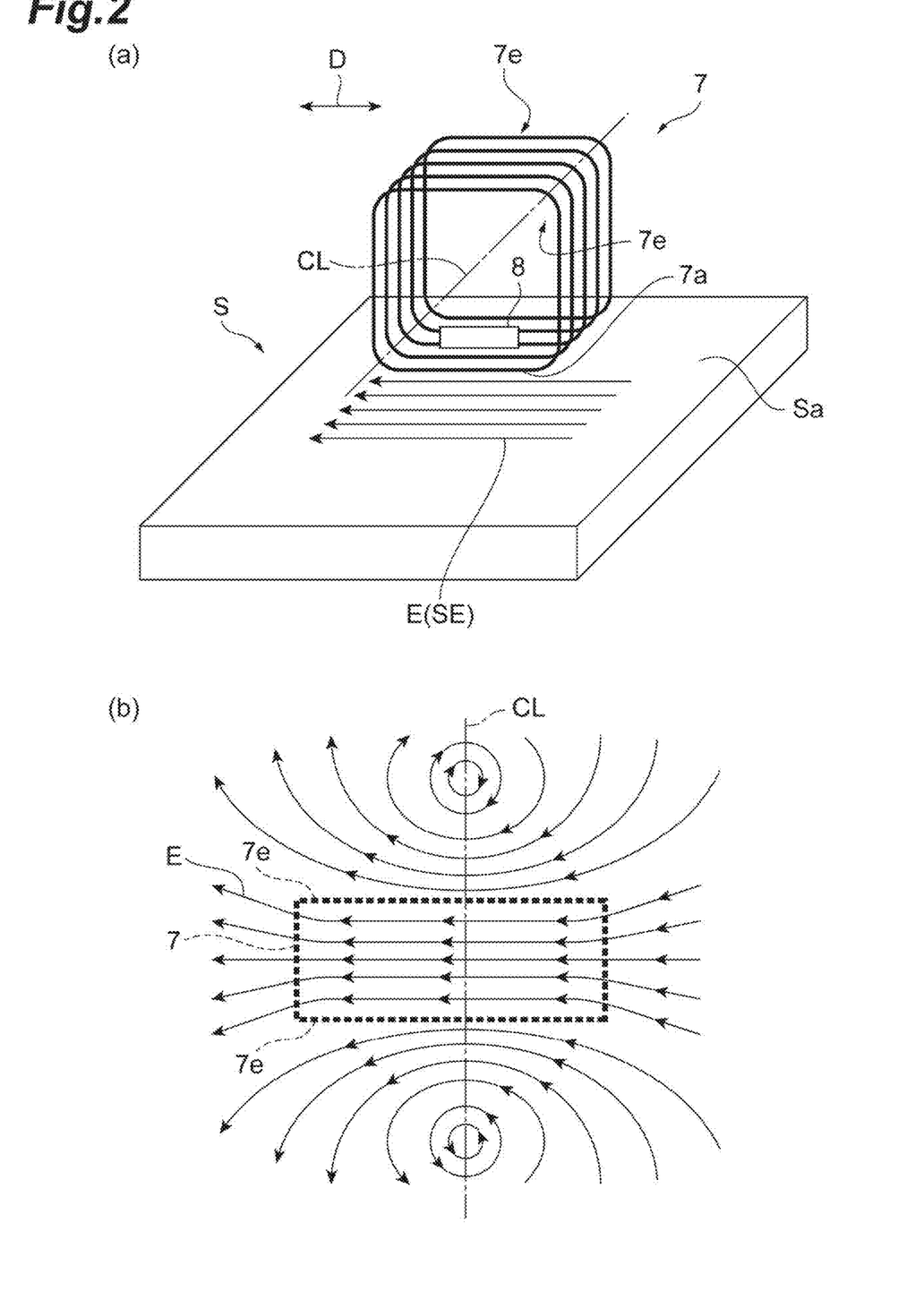
FIG. 2(a) is a diagram illustrating general configurations of a coil and a magnetic field sensor.
FIG. 2(b) is a diagram illustrating eddy currents formed by the coil.

To be specific, as illustrated in FIG. 2(a), the coil 7 is disposed at the position opposite to the surface Sa of the specimen S. The coil 7 is disposed at a position away from the surface Sa of the specimen S (here, a position spaced above the surface Sa). The coil 7 is wound around a winding axis CL extending along the surface Sa. The winding axis CL of the coil 7 extends parallel to the surface Sa, and here extends in a direction orthogonal to the direction of each of the conductive fibers SE that are the targets for checking whether the meandering is present. Coil faces 7e of the coil 7 are disposed to be perpendicular to the surface Sa of the specimen S. However, the "perpendicularity" mentioned here need not strictly be 90°, and may be an angle including an error or the like concerning installation. The coil faces 7e correspond to opposite end faces in a direction of the winding axis CL among faces of the coil 7.

Figure 3:
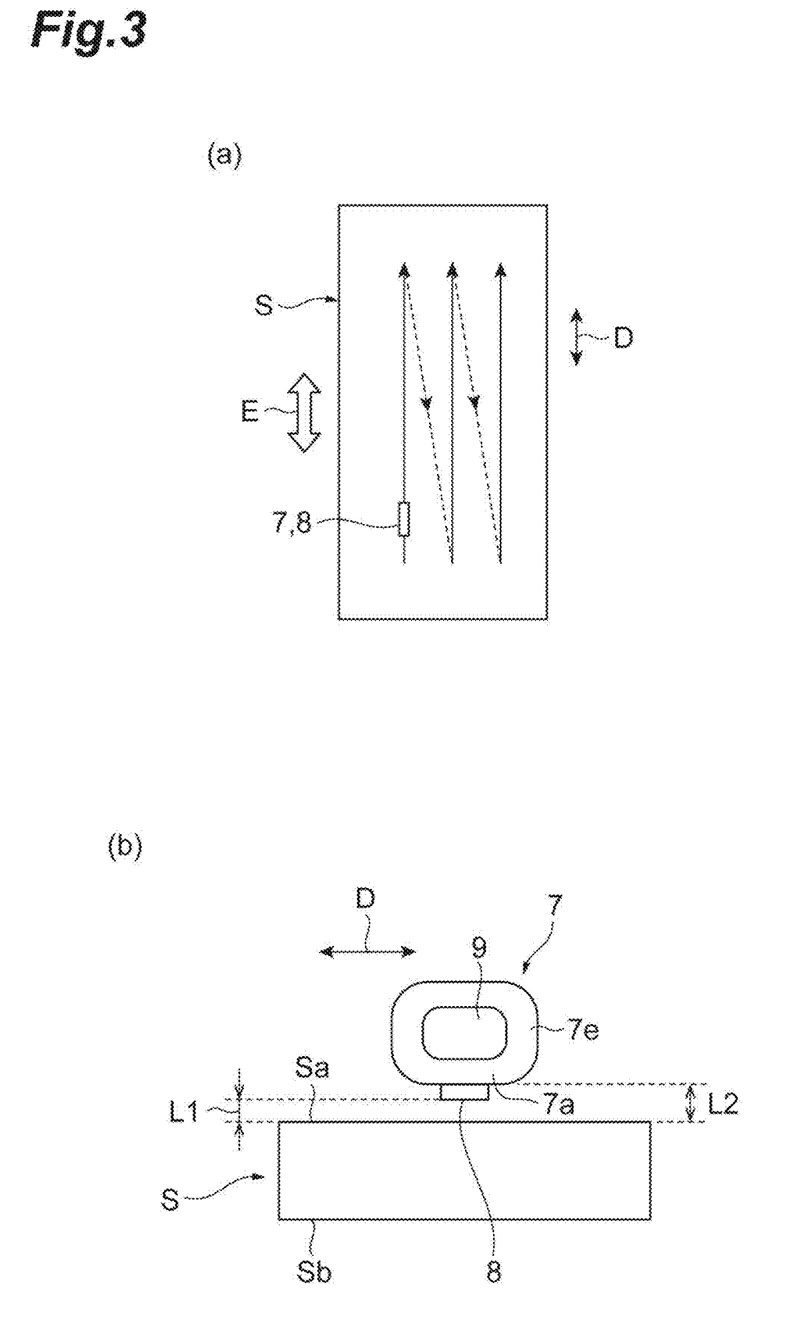
FIG. 3(a) is a diagram illustrating scanning directions of the coil and the magnetic field sensor.
FIG. 3(b) is a general configuration diagram of the coil and the magnetic field sensor viewed in a transverse direction.

As illustrated in FIG. 2(b), the coil 7 generating a magnetic field approaches the surface Sa, and thereby eddy currents occur around the coil 7 due to an electromagnetic induction effect. An eddy current (clockwise rotation in the figure) centered on a position of one side (an upper side in the figure) of the winding axis CL with respect to the coil 7 occurs, and an eddy current (counterclockwise rotation in the figure) centered on a position of the other side (a lower side in the figure) of the winding axis CL occurs. The eddy currents created at two places in a region of the surface Sa which faces the coil 7 join and pass toward one side (a left side in the figure). As described above, the eddy currents occur on the surface Sa of the specimen S which relates to the region facing the coil 7, and a current E flows in a direction that is approximately parallel to the coil faces 7e (a direction that is nearly orthogonal to the winding axis CL). When viewed from the top, the coil faces 7e and the conductive fibers SE may not be completely parallel to each other, and may deviate, for instance, within a range of −45 to +45°. In the present embodiment, the coil 7 is formed by winding a conductive wire around the winding axis CL in an approximately rectangular shape. Therefore, each of four ends of the coil 7 extends in a straight line shape. Especially, an end 7a (here, a lower end) of the coil 7 which faces the surface Sa of the specimen S extends in parallel along the surface Sa. As illustrated in FIG. 3(a), the end 7a of the coil 7 is spaced apart from the surface Sa of the specimen S by a dimension L2. The dimension L2 may be set to, for instance, 0 to 5 mm. A core 9 may be disposed inside the coil 7. The core 9 may be formed of ferrite, a silicon steel sheet, or the like. A frequency of the current flowing to the coil 7 ranges from 10 kHz to 20 MHz. Conductivity of a carbon fiber reinforced plastic (CFRP) in a planar direction of the CFRP differs according to a material, and is about 25000 S/m in this example. Considering a skin depth, the skin depth becomes 30 mm when the frequency of the current flowing to the coil 7 is 10 kHz, and becomes 300 μm when the frequency is 100 MHz. Accordingly, the frequency of the current flowing to the coil 7 may range from 10 kHz to 100 MHz.

The magnetic field sensor 8 is a sensor for measuring a magnetic field. To be specific, as the magnetic field sensor 8, an MI sensor, a GMR sensor, a TMR sensor, an AMR sensor, an FG sensor, a Hall element, an SQID sensor, a coil, or the like may be adopted. The magnetic field sensor 8 is disposed at a position at which it faces the surface Sa of the specimen S. In the present embodiment, the magnetic field sensor 8 is provided between the surface Sa and the facing coil 7. The magnetic field sensor 8 is provided on a lower end face of the end 7a of the coil 7 which faces the surface Sa of the specimen S. As illustrated in FIG. 3(a), a lower end of the magnetic field sensor 8 is spaced apart from the surface Sa of the specimen S by a dimension L1. The dimension L1 may be set to, for instance, 0 to 5 mm.

A direction D of a magnetosensitive axis of the magnetic field sensor 8 extends along the surface Sa, and extends in a direction that intersects (here, is orthogonal to) the winding axis CL. The direction D of the magnetosensitive axis of the magnetic field sensor 8 is horizontal with the surface Sa, and is parallel to the coil faces 7e. The direction D of the magnetosensitive axis is approximately identical to the direction in which the current flows. Here, the direction D of the magnetosensitive axis of the magnetic field sensor 8 is directed in a direction in which the conductive fibers SE extend (the direction in which the current flows). The direction D of the magnetosensitive axis may not be completely parallel to the coil faces 7e (that is, may not be completely orthogonal to the winding axis CL), and may deviate, for instance, within a range of −6 to +6°.

Figure 5:
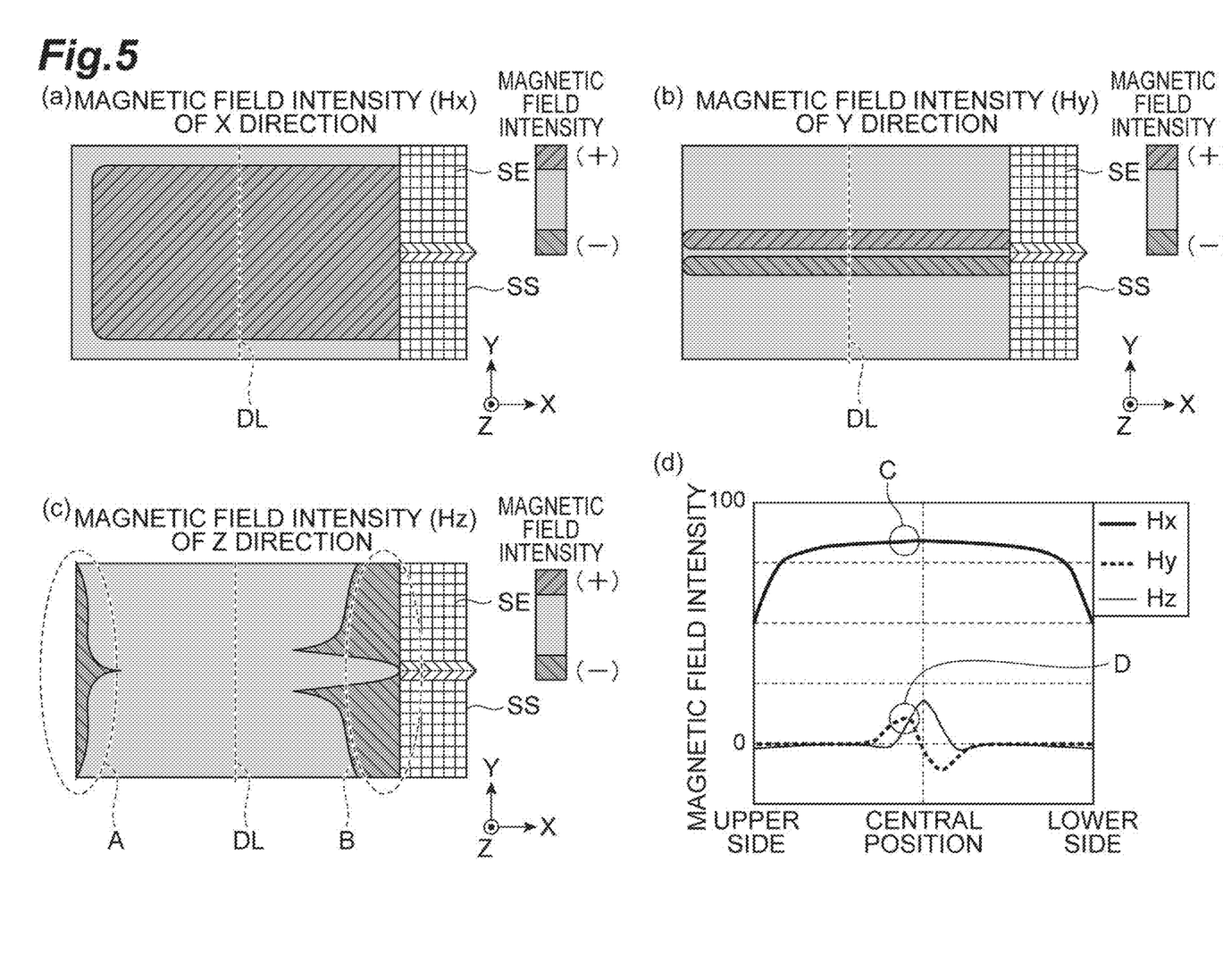
FIGS. 5(a), 5(b), and 5(c) are diagrams showing magnetic field intensity in each direction.
FIG. 5(d) is a graph showing the magnetic field intensity at a position of line DL.

The direction D of the magnetosensitive axis of the magnetic field sensor 8 is preferably parallel to the coil faces 7e (here, is directed in the direction in which the conductive fibers SE extend), which will be described with reference to FIG. 5. In FIG. 5, when a simulation is performed on the assumption that a current is applied in a direction of the Y axis of a specimen having a meandering portion, an image of a simulation result showing a distribution of magnetic field intensity in a direction of each axis on a surface of the specimen is illustrated. This simulation does not partly generate the eddy currents using the coil as in the embodiment, but causes a current of uniform intensity in a direction of the X axis to flow in the direction of the Y axis. FIG. 5(a) shows distribution of magnetic field intensity Hx of the direction of the X axis, and FIG. 5(b) shows distribution of magnetic field intensity Hy of the direction of the Y axis. FIG. 5(c) shows distribution of magnetic field intensity Hz of a direction of the Z axis. In the figures, a portion indicated by hatching is a portion at which an absolute value of the magnetic field intensity is great. Fibrous directions of the conductive fiber fabric SS and the conductive fibers SE are shown at the right end of each figure. The direction of the Y axis is the fibrous direction, and the direction of the Z axis is a direction of lamination. The direction of the X axis is a direction that is orthogonal to the fibrous direction. The conductive fibers SE of the conductive fiber fabric SS meander at a central position in the direction of the Y axis. FIG. 5(d) is a graph showing the magnetic field intensity in the direction of each axis on a line DL indicated in each figure. This results in plotting values of the magnetic field intensity obtained by the simulation. Referring to the results of FIG. 5, portions at which a change in the magnetic field intensity in the direction of each axis appeared were observed. Whether or not the change of the magnetic field intensity appeared was determined by whether or not the portion at which the absolute value of the magnetic field intensity was greater (the portion indicated by hatching) compared to a surrounding region in viewing distribution of colors of FIGS. 5(a), 5(b), and 5(c) was locally generated. Alternatively, whether or not the change of the magnetic field intensity appeared was determined by whether or not a graph of the magnetic field intensity in the graph of FIG. 5(d) increased or decreased locally, and thereby a maximum point or a minimum point having a magnitude greater than or equal to a predetermined absolute value appeared. According to the results shown in FIG. 5, the change of the magnetic field intensity appears at the meandering portion along with Hy and Hz. However, the magnetic field intensity Hz is changed at ends A and B shown in FIG. 5(c) regardless of the meandering (it is observed that the absolute value of the magnetic field intensity is locally increased). Thus, the direction D of the magnetosensitive axis of the magnetic field sensor 8 is preferably set to the direction of the Y axis, that is, the direction in which the current flows (the direction that is approximately parallel to the coil faces 7e).

Figure 8:
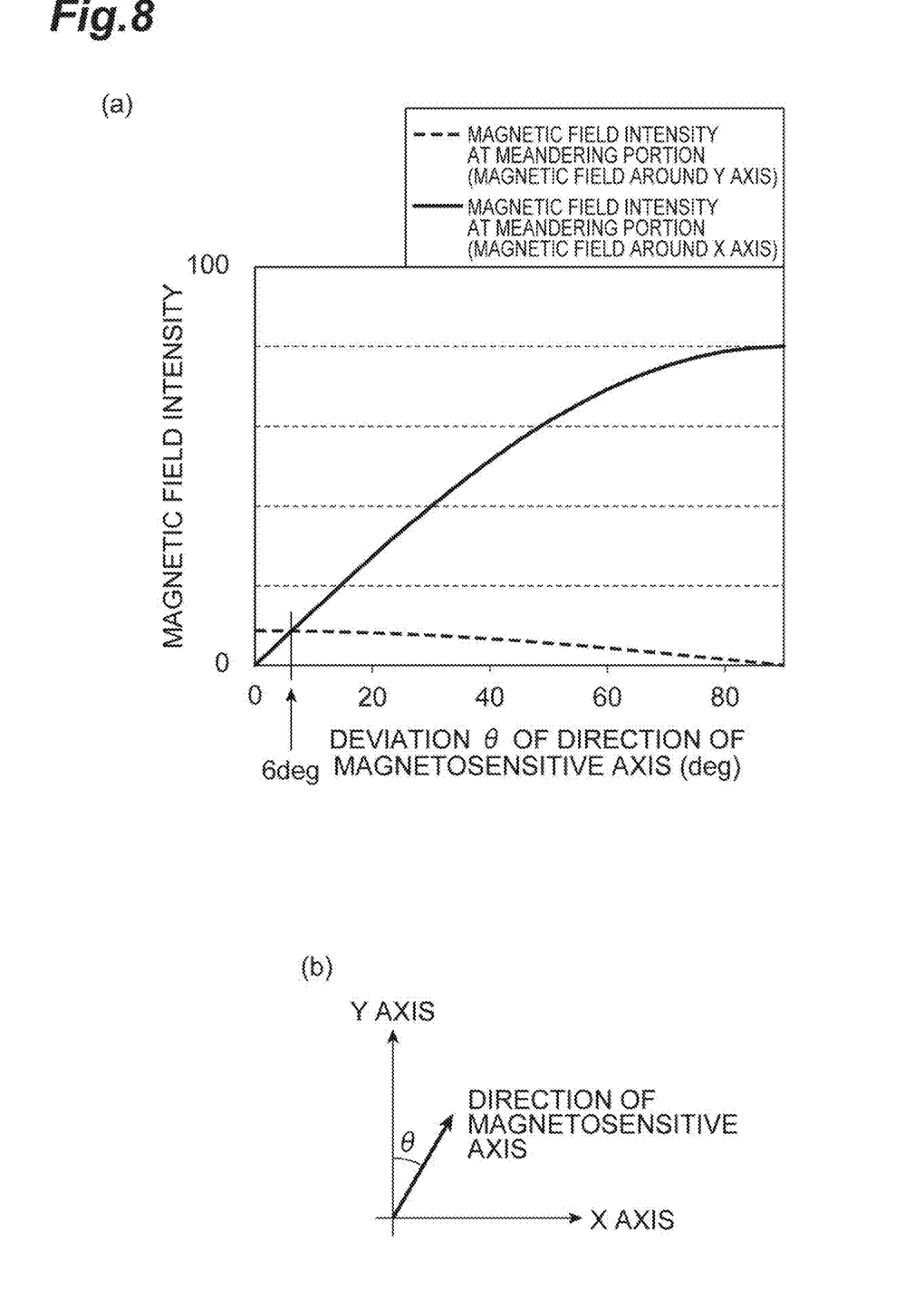
FIG. 8 is a graph illustrating a relation between the direction of the magnetosensitive axis and the magnetic field intensity.

The point that the direction D of the magnetosensitive axis may deviate from the coil faces 7e within a range of −6 to +6° will be described with reference to FIG. 8. FIG. 8(a) is a graph showing the magnetic field intensity at the meandering portion. FIG. 8(a) is a graph showing the magnetic field intensity at the meandering portion (formed at a position indicated by "D" that is a maximum point of "Hy" in FIG. 5(d)). In FIG. 8(a), a solid line indicates the magnetic field intensity around the X axis, and a broken line indicates the magnetic field intensity around the Y axis. The longitudinal axis of FIG. 8(a) indicates the magnetic field intensity, and the transverse axis indicates deviation θ of the direction D of the magnetosensitive axis with respect to the Y axis. The deviation θ of the direction D of the magnetosensitive axis is an angle shown in FIG. 8(b). As indicated by the broken line, the magnetic field intensity around the Y axis when "θ=0°" is equal to the magnetic field intensity at the maximum point of "D" shown in FIG. 5(d). When θ increases to become "θ=90°," the direction of the magnetosensitive axis does not have a component of the direction of the Y axis regardless of measuring the magnetic field intensity around the Y axis, and thus the magnetic field intensity becomes 0. As indicated by the solid line, the magnetic field intensity around the X axis when "θ=0°" becomes 0 regardless of measuring the magnetic field intensity around the X axis because the direction of the magnetosensitive axis does not have a component of the direction of the X axis. When θ increases to become "θ=90°," the magnetic field intensity is equal to the magnetic field intensity at "C" shown in FIG. 5(d). The magnetic field intensity of the solid line is increased to draw a sine curve. When these graphs are drawn, the graphs intersect when "θ=6°." It is understood from these graphs that, when θ exceeds 6°, a magnetic field around the X axis becomes dominant over a magnetic field around the Y axis regardless of measuring the magnetic field intensity around the Y axis. Accordingly, if the direction D of the magnetosensitive axis is within the range of −6 to +6° from the coil faces 7e, the magnetic field around the Y axis can be made dominant over the magnetic field around the X axis.

When the targets for checking whether the meandering is present are used as the plurality of prepregs $S_1, S_3, \ldots, S_{n-1}$, the current flows in directions (directions that are orthogonal to the shown longitudinal directions) of the conductive fibers SE in each of the conductive fiber fabrics SS. To this end, the directions of the coil 7 and the magnetic field sensor 8 are changed to 90° from the case in which the plurality of prepregs $S_2, S_4, \ldots, S_n$ are used as the targets for checking whether the meandering is present. However, the coil 7 may be installed such that the eddy currents occur along the conductive fibers SE concerning the targets to be measured, and an angle between each of the prepregs $S_1, S_3, \ldots, S_{n-1}$ and each of the prepregs $S_2, S_4, \ldots, S_n$ may be 0° or ±45°.

Next, a procedure of the method for detecting meandering of fibers, in which it is checked whether the meandering of the conductive fibers SE in the specimen S is present using the device 1 for detecting meandering of fibers, will be described. First, when the current applying unit 4 applies a current to the coil 7 disposed at a position at which it faces the surface Sa of the specimen S, the current flows in directions (a direction of an outlined thick arrow of FIG. 3(a)) of the conductive fibers SE in each of the conductive fiber fabrics 55 of the plurality of prepregs $S_2, S_4, \ldots, \ldots, S_n$ that are the targets for checking whether the meandering is present.

The magnetic field sensor 8, the direction D of the magnetosensitive axis of which is matched with the direction of the thick arrow of FIG. 3(a) scans the specimen S along the arrow along with the coil 7, by operating the stage 2 on which the specimen S is placed in this state. At this time, as illustrated in FIG. 3(b), the magnetic field sensor 8 is spaced apart from the specimen S by a dimension L1 (holds a liftoff amount L1) and scans the specimen S.

Figure 4:
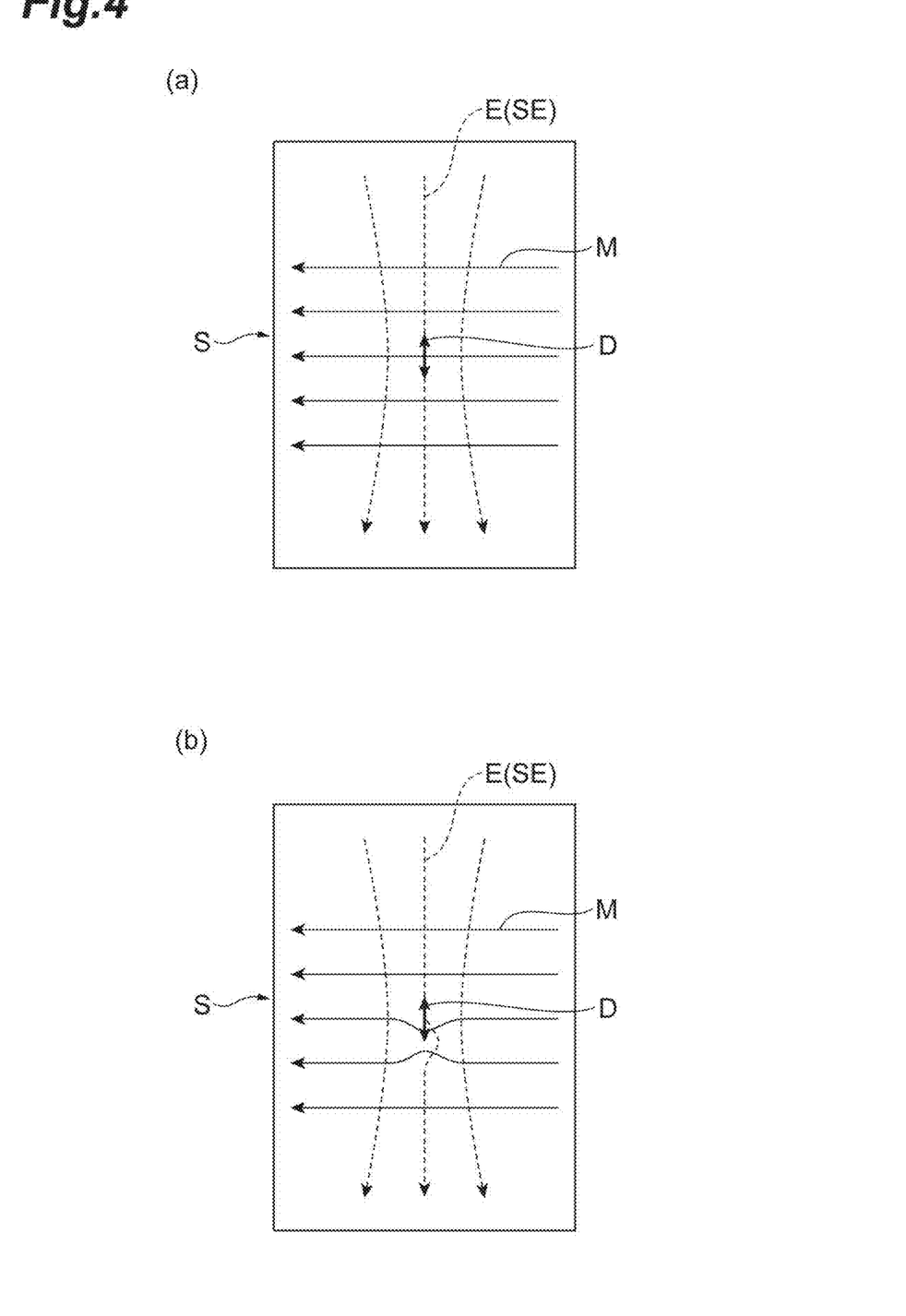
FIG. 4 is a diagram illustrating a relation between a direction of a magnetosensitive axis and a direction of a current, wherein (a) illustrates a state in which conductive fibers do not meander, and (b) illustrates a state in which the conductive fibers meander.

With regard to this scanning, when the meandering of the conductive fibers SE is not present, the current flows straight along straight arrangement of the conductive fibers SE on the surface of the specimen S as illustrated in FIG. 4(a). Since the current flows straight in this way, no disorder occurs at a magnetic field M created from the eddy currents. Therefore, no change is detected in the magnetic field M by the magnetic field sensor 8. On the other hand, when the meandering of the conductive fibers SE is present, the current flows along a portion at which the arrangement disorder of the conductive fibers SE is present on the surface of the specimen S, and thus the current is fluctuated by the portion as illustrated in FIG. 4(b). In this case, as the current is locally fluctuated, the disorder also occurs at the magnetic field M created from the eddy currents. When the disorder occurs at the magnetic field M created locally in this way, the magnetic field sensor 8 detects the change of the magnetic field M. Detecting any state as the "change of the magnetic field" is not particularly limited. For example, when the magnetic field sensor 8 detects a peak value of the magnetic field intensity, it may be determined that the change of the magnetic field M occurs. In this case, when the magnetic field intensity having a smaller wavelength than a predetermined threshold and a greater absolute value than a predetermined threshold is detected, it may be determined that the change of the magnetic field occurs. Alternatively, when a waveform of the magnetic field intensity detected by the magnetic field sensor 8 is distorted and a magnitude of variation of a cycle of the waveform is greater than or equal to a predetermined threshold, it may be determined that the change of the magnetic field M occurs.

The controller 6 determines a portion at which the magnetic field sensor 8 detects the change of the magnetic field as a portion at which the meandering occurs at the conductive fibers SE of the plurality of prepregs $S_2, S_4, \ldots, S_n$ that are the targets for checking whether the meandering is present. In this way, the meandering portion is adapted to be detected by scanning of the coil 7 and the magnetic field sensor 8 that can be displaced without contact with the specimen S. Therefore, without partly or minutely cutting the specimen S, the meandering of the conductive fibers SE can be detected, or conditions of the conductive fibers SE in the entire specimen S can be checked.

Next, an operation and effects of the method for detecting meandering of fibers in a conductive composite material according to the present embodiment will be described.

In the method for detecting meandering of fibers in a conductive composite material according to the present embodiment, the coil is disposed at a position at which it faces the surface Sa of the conductive composite material such that the coil faces 7e are perpendicular to the surface, and thereby the eddy currents can be created at the conductive composite material. In this way, the coil 7 is disposed at a position at which it faces the conductive composite material, and thereby the current can be applied to the conductive composite material. Thus, work or the like for attaching electrodes to the conductive composite material is not required. Accordingly, the meandering (the arrangement disorder) of the fibers of the conductive composite material can be easily detected. Here, as a result of earnest study, the inventors of this disclosure found that the magnetic field sensor 8 was disposed such that the direction D of the magnetosensitive axis was horizontal with the surface Sa of the conductive composite material and was parallel to the coil faces 7e, and thereby the meandering portion of the fibers could be accurately detected compared to when the direction of the magnetosensitive axis was set to be another direction. The method for detecting meandering of fibers in a conductive composite material according to the present embodiment includes a step of disposing the magnetic field sensor 8 at a position at which the magnetic field sensor 8 faces the surface Sa of the conductive composite material such that the direction D of the magnetosensitive axis is horizontal with the surface Sa and is parallel to the coil faces 7e. Accordingly, the magnetic field sensor 8 measures the magnetic field, and thereby the meandering portion of the conductive composite material can be accurately detected. Thus, the meandering of the fibers of the conductive composite material can be easily and accurately detected. The device 1 for detecting meandering of fibers according to the present embodiment can also exert the same operation and effects.

In the method for detecting meandering of fibers in a conductive composite material according to the present embodiment, the magnetic field sensor 8 is provided between the surface Sa and the facing coil 7. Thereby, the magnetic field sensor 8 can more accurately detect a change in the magnetic field.

In the method for detecting meandering of fibers in a conductive composite material according to the present embodiment, the ends of the coil 7 which face the surface Sa of the conductive composite material extend along the surface. Thereby, the eddy currents caused by the coil 7 are easily created at the conductive composite material.

In the method for detecting meandering of fibers in a conductive composite material according to the present embodiment, the frequency of the current flowing to the coil 7 ranges from 10 kHz to 20 MHz. Thereby, the eddy currents caused by the coil 7 are easily created at the conductive composite material.

The present disclosure is not limited to the above embodiment.

In the above embodiment, the specimen S formed by alternately laminating the plurality of sheets of prepregs $S_1$, $S_3$, ..., $S_{n-1}$, and $S_2$, $S_4$, ..., $S_n$ having a difference of 90° between the directions of fiber orientation is shown. Alternatively, for example, a specimen formed by alternately laminating a plurality of sheets of prepregs having an angle of ±45° between the directions of fiber orientation may be adopted, or a specimen formed by laminating a plurality of sheets of prepregs, all of which have the same direction of fiber orientation, may be adopted.

Figure 7:
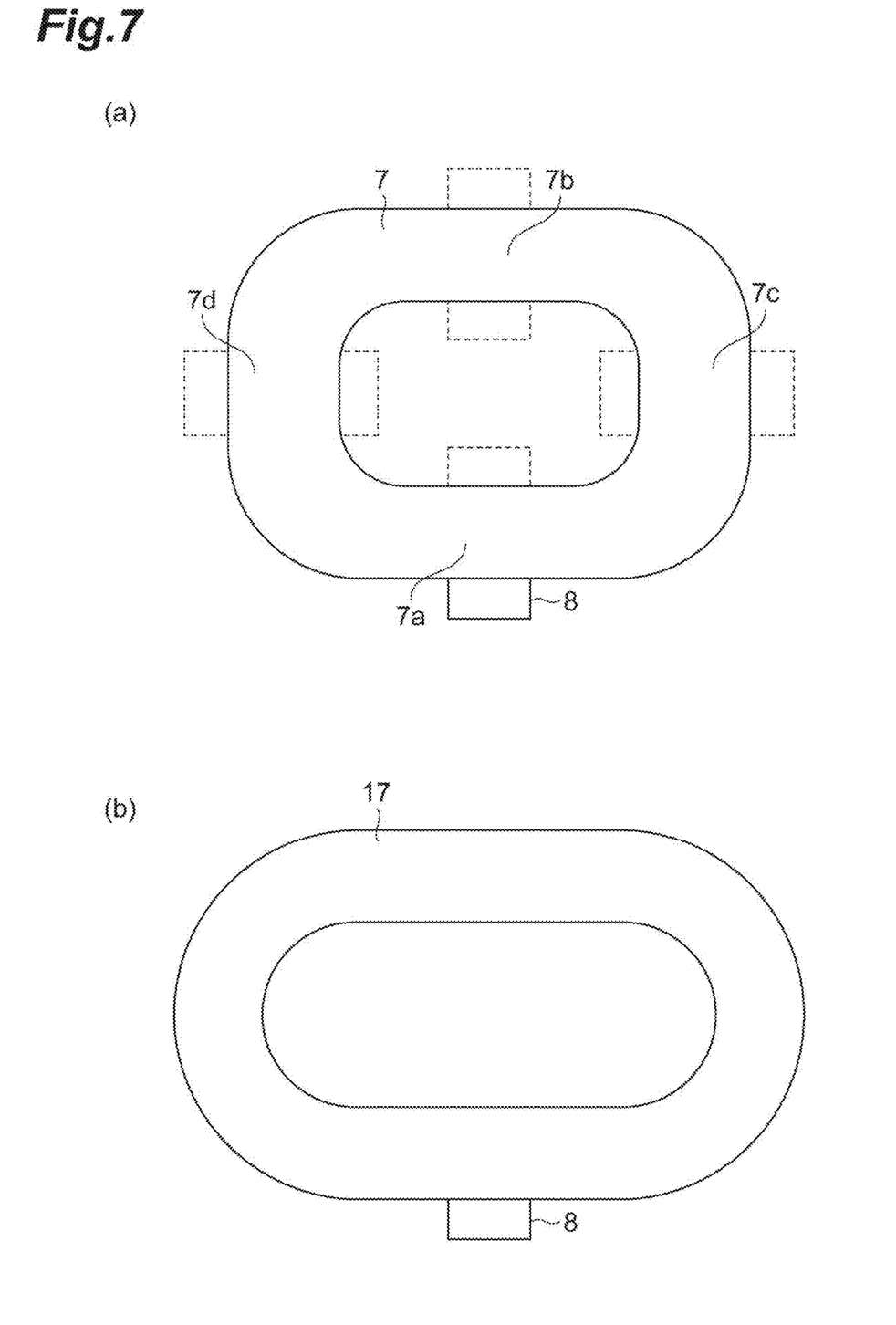
FIG. 7 is a diagram illustrating a coil and a magnetic field sensor according to a modification.

The disposition of the magnetic field sensor is not limited to the above embodiment. For example, as illustrated in FIG. 7(a), when the coil 7 has ends 7b, 7c, and 7d other than the end 7a, the magnetic field sensor may be provided at these ends 7b, 7c, and 7d as indicated by a broken line. The magnetic field sensor may not be provided at an outer circumference side of the coil 7, and may be provided at an inner circumference side of the coil 7 as indicated by the broken line in the figure. A plurality of magnetic field sensors may be provided with respect to one coil 7. The shape of the coil is not limited to the approximately rectangular shape as in the embodiment, and may adopt any shape. For example, a coil 17 having an oval shape as illustrated in FIG. 7(b) may be adopted. Alternatively, an elliptic shape, a true circle shape, other polygonal shapes, etc. may be adopted.

EXAMPLES

Hereinafter, the method for detecting meandering of fibers in a conductive composite material according to an embodiment of the present disclosure will be described on the basis of examples, but the method is not limited to the following examples.

Figure 6:
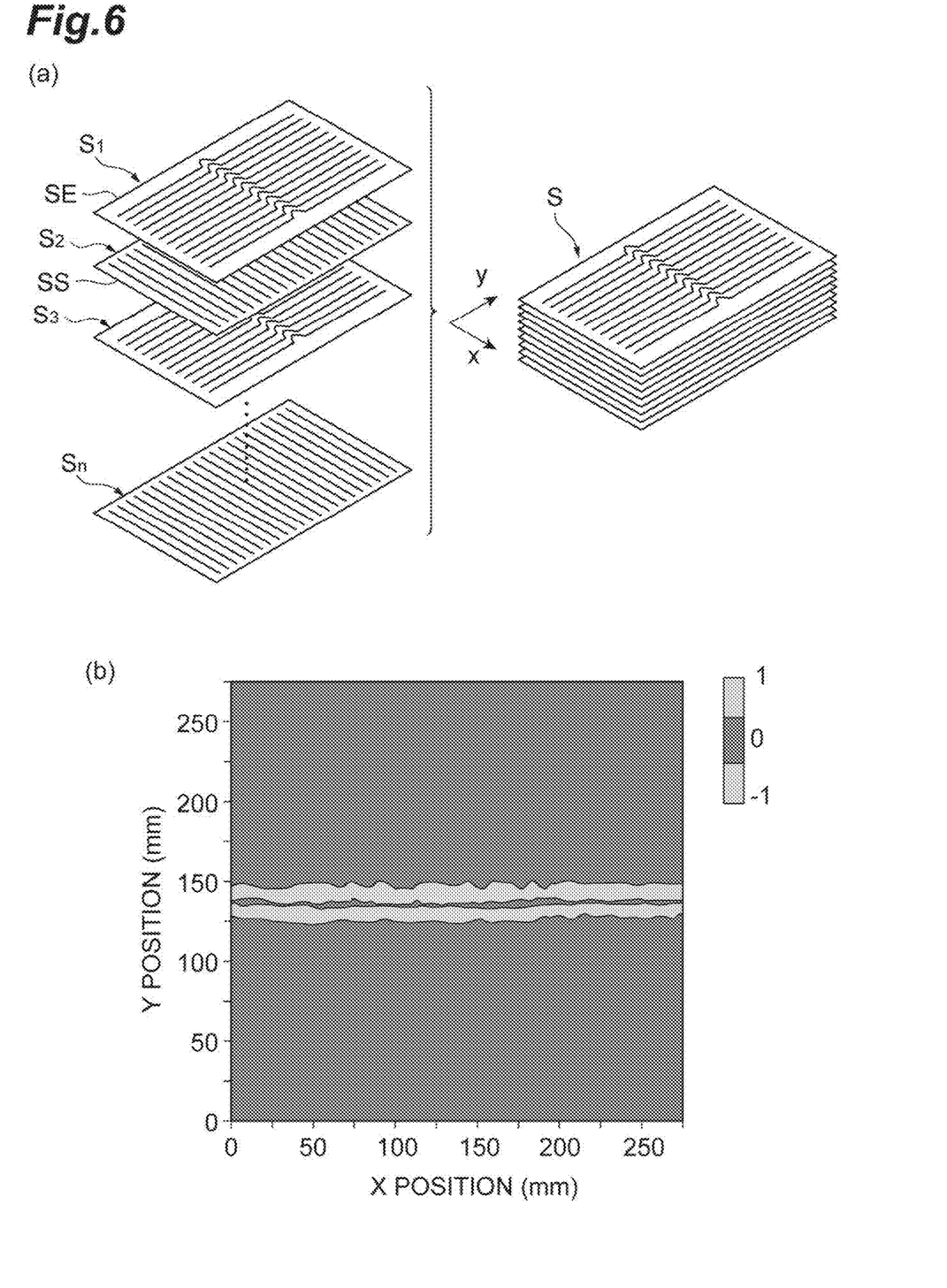
FIG. 6(a) illustrates a configuration of the conductive composite material used in an example.
FIG. 6(b) is a diagram illustrating test results of the example.

As illustrated in FIG. 6(a), a specimen in which conductive fibers were forced to artificially meander was prepared. A thickness of the specimen was 2 mm, and conductive fiber fabrics were laminated such that fibrous directions of the conductive fibers deviated by 90° for each layer. A coil and a magnetic field sensor were disposed as illustrated in FIG. 3(b). An exciting coil having a thickness of 1 mm and an outer size of 5.2 mm×4.2 mm was used as the coil. An MI sensor was used as the magnetic field sensor. A test frequency was set to 1 MHz, and an applied voltage to the coil was set to ±20 V. A magnetic field signal detected by the magnetic field sensor was detected by a lock-in amplifier, and an amplitude and a phase were measured. The phase was adjusted with respect to the detected signal such that an output signal is maximized at a meandering introduction portion. Scanning was performed by the magnetic field sensor and the coil along a track as illustrated in FIG. 3(a). A scanning speed was set to 50 mm/s, a scan pitch in a transverse direction was set to 1 mm, and a recording pitch in a longitudinal direction was set to 0.5 mm.

Measured results obtained by the above test are shown in FIG. 6(b). An image of FIG. 6(b) shows the measured results when the magnetic field intensity in the direction of the Y axis within a range of a square of 275 mm from an end of the specimen is measured. Artificial meandering is introduced in the vicinity of the middle of the specimen in the direction of the Y axis. A signal voltage is low at a portion at which the meandering occurs, a dark color is given. In contrast, the signal voltage is high at a portion at which the meandering occurs, and a faint color is given. Thus, it is understood that the meandering of the conductive fibers can be detected by the method according to the example.

REFERENCE SIGNS LIST

1 Device for detecting meandering of fibers
6 Controller (detector)
7, 17 Coil
8 Magnetic field sensor (magnetic field measuring unit)
S Specimen (conductive composite material)
SS Conductive fiber fabric
Sa Surface
D Direction of magnetosensitive axis
CL Winding axis

What is claimed is:

1. A method for detecting arrangement disorder of fibers in a conductive composite material using conductive fibers, the method comprising:
   a step of disposing a coil at a position at which the coil faces a surface of the conductive composite material such that a coil face is perpendicular to the surface;
   a step of disposing a magnetic field measuring unit at a position at which the magnetic field measuring unit faces the surface of the conductive composite material such that a direction of a magnetosensitive axis is horizontal with the surface and is parallel to the coil face; and
   a step of detecting a portion at which the arrangement disorder of the fibers in the conductive composite material is present by measuring a magnetic field with the magnetic field measuring unit.

2. The method according to claim 1, wherein the magnetic field measuring unit is provided between the surface of the conductive composite material and the coil facing the surface.

3. The method according to claim 1, wherein an end of the coil which faces the surface of the conductive composite material extends along the surface.

4. The method according to claim 2, wherein an end of the coil which faces the surface of the conductive composite material extends along the surface.

5. The method according to claim 1, wherein a frequency of a current flowing to the coil ranges from 10 kHz to 20 MHz.

6. The method according to claim 2, wherein a frequency of a current flowing to the coil ranges from 10 kHz to 20 MHz.

7. The method according to claim 3, wherein a frequency of a current flowing to the coil ranges from 10 kHz to 20 MHz.

8. The method according to claim 4, wherein a frequency of a current flowing to the coil ranges from 10 kHz to 20 MHz.

9. A device for detecting arrangement disorder of fibers in a conductive composite material using conductive fibers, the device comprising:
   a coil disposed at a position at which the coil faces a surface of the conductive composite material such that a coil face thereof is perpendicular to the surface;
   a magnetic field measuring unit disposed at a position at which the magnetic field measuring unit faces the surface of the conductive composite material such that a direction of a magnetosensitive axis is horizontal with the surface and is parallel to the coil face; and
   a detector for detecting a portion at which the arrangement disorder of the fibers in the conductive composite material is present by measuring a magnetic field with the magnetic field measuring unit.

* * * * *